United States Patent [19]
Zettlmeissl et al.

[11] Patent Number: 5,700,663
[45] Date of Patent: *Dec. 23, 1997

[54] MUTANTS OF HUMAN ANTITHROBIN III AND METHODS FOR THEIR PRODUCTION

[75] Inventors: Gerd Zettlmeissl, Lahntal; Hermann Erich Karges, Marburg; Achim Becker, Dautphetal, all of Germany

[73] Assignee: Behringwerke Aktiengesellschaft, Marburg, Germany

[*] Notice: The term of this patent shall not extend beyond the expiration date of Pat. No. 5,618,713.

[21] Appl. No.: 452,836

[22] Filed: May 30, 1995

Related U.S. Application Data

[62] Division of Ser. No. 993,910, Dec. 18, 1992, Pat. No. 5,618,713, which is a continuation of Ser. No. 469,913, Jan. 22, 1990, abandoned.

[30] Foreign Application Priority Data

Jan. 24, 1989 [DE] Germany ................. 39 01 917.9

[51] Int. Cl.⁶ ................. A61K 38/17; C07K 14/47
[52] U.S. Cl. ................. 435/69.6; 435/226; 530/380; 514/12
[58] Field of Search ................. 435/69.6, 226, 435/172.3; 514/12; 530/380, 395, 350

[56] References Cited

U.S. PATENT DOCUMENTS 4,632,981  12/1986  Bock ................. 530/393

FOREIGN PATENT DOCUMENTS 0 090 505 A2  10/1983  European Pat. Off. .
0 256 302 A2   2/1988  European Pat. Off. .
36 24 453 A1   1/1988  Germany .

OTHER PUBLICATIONS

Zettlmeissl et al., "Influence of Glycosylation on the Functional Properties of Human Therapeutic Plasma Proteins", Protein Glycosylation: Cellular, Biotechnological and Analytical Aspects, GBF Monographs, vol. 15 (ed. H.S. Conradt), pp. 259–268, 1991.
Bowie et al., "Deciphering the Message in Protein Sequences: Tolerance to Amino Acid Substitutions", Science, vol. 247, pp. 1306–1310, Mar. 1990.
J. Schrader et al., "Chromogene Substratmethoden zur Antithrombin III-Bestimmung", Des Arztliche Laboratorium, pp. 111–114, (1986).
G. Zettlmeissl et al., "Expression of Biologically Active Human Anti-thrombin III in Chinese Hamster Ovary Cells", Bio/Technology, vol. 5, pp. 720–725 (Jul. 1987).
M. Hoylaerts et al., "Involvement of Heparin Chain Length in the Heparin-catalyzed Inhibition of Thrombin by Antithrombin III", J. Biol. Chem., vol. 259, No. 9, pp. 5670–5677 (May 1984).
C. Peterson et al., "Isolation and Characterization of an Antithrombin III Variant with Reduced Carbohydrate Content and Enhanced Heparin Binding", J. Biol. Chem., vol. 260, No. 1, pp. 610–615 (Jan. 1985).
S. Brennan et al., "Physiological Variant of Antithrombin-III Lacks Carbohydrate Sidechain at Asn 135", FEBS Letters, vol. 219, No. 2, pp. 431–436 (Jul. 1987).
Yansushi Morinaga et al., "Improvement of Oligonucleotide-Directed Site-Specific Mutagenesis Using Double-Stranded Plasmid DNA", Bio/Technology, pp. 636–639 (Jul. 1984).
Jorgensen et al., Biochem. J. 231; 59–63 (1985).
Molho-Sabatier et al., J. Clin. Invest. 84; 1236–1242 (1989).
W. Kramer et al., "The Gapped Duplex DNA Approach to Oligonucleotide-Directed Mutation Construction", Nucl. Acids Res., vol. 12, No. 24, pp. 9441–9456 (1984).
G. Zettlmeissl et al., "Efficient Expression System for Human Antithrombin III in Baby Hamster Kidney Cells", Behring Inst. Mitt., No. 82, pp. 26–34 (1988).
F. Sanger et al., "DNA Sequencing with Chain-Terminating Inhibitors", Proc. Natl. Acad. Sci. USA, vol. 74, No. 12, pp. 5463–5467. (1977).
A. Hensen et al., "III. Antithrombin III Assay", Thromb. Diatl. Haemorrh.,vol. 9, pp. 18–29 (1963).
J. Schrader et al., "Methoden zur Bestimmung des Antithrombin III (Methods for the Determination of Antithrombin III)", Arztl. Lab., vol. 29, pp. 35–39 (1983).
S. Engelbrecht et al., "Separation of Human Leucocyte Enzymes Alaine Aminopeptidase, Cathepsin G, Collagenase, Elastase and Myeloperoxidase", Hoppe–Seyler's Z. Physiol. Chem., vol. 363, pp. 305–315 (Mar. 1982).
K. Nakajima et al., "Mapping the Extended Substrate Binding Site of Cathepsin G an dHuman Leukocyte Elastase", J. Biol. Chem., vol. 254, No. 10, pp. 4027–4031 (May 1979).

*Primary Examiner*—Charles L. Patterson, Jr.
*Attorney, Agent, or Firm*—Finnegan, Henderson, Farabow, Garrett & Dunner, L.L.P.

[57] ABSTRACT

Mutants of AT III which have been advantageously modified at one or more potential glycosylation sites or at the Arg393 position are described. As a rule, combination of the mutations enhances the advantageous modifications.

5 Claims, No Drawings

MUTANTS OF HUMAN ANTITHROMBIN III AND METHODS FOR THEIR PRODUCTION

This is a division of application Ser. No. 07/993,910, filed Dec. 18, 1992, now U.S. Pat. No. 5,681,713, which is a continuation of Ser. No. 07/469,913, filed Jan. 22, 1990, now abandoned.

The invention relates to mutants of AT III which have improved properties by comparison with wild-type AT III. Modification at one or more potential glycosylation sites (for example Asn 135, Asn 155) increases the heparin-binding/heparin-activating properties while retaining the protease specificity of AT III. Alterations at the position Arg 393 result in alterations in the specificity towards proteases. As a rule, combination of the mutations enhances the improvements.

The cDNA coding for human antithrombin III (AT III) and the expression thereof in *E. coli* are described in European Patent Application EP 0 090 505 A2. Expression of AT III is additionally shown in recombinant yeasts (EP 0 256 302 A2) and mammalian cells (DE 3 624 453 A1). It emerged from these experiments that only AT III secreted by mammalian cells into the culture medium shows complete biological activity in vitro and has a complex carbohydrate structure very similar to the plasma protein (Zettlmeissl et al., BioTechnology, 1987, 5, 720–725).

The molecular weight of about 58 kd of recombinant AT III from mammalian cells corresponds to that of the protein purified from plasma. The amino acid sequence of mature human AT III is depicted in Tab. 1.

AT III is a member of the serpin family of proteins and accordingly has great homology to protease inhibitors such as alpha-1 antitrypsin, alpha-2 antiplasmin, heparin cofactor II, alpha-1 antichymotrypsin, plasminogen activator inhibitor etc. When the serine protease thrombin interacts with AT III it cleaves the Arg393-Ser394 bond and there is formation of a covalent AT III-thrombin complex. Thrombin loses its protease activity on complexation. In the absence of heparin, AT III is a relatively poor inhibitor of thrombin. Optimal concentrations of heparin increase the rate constant of the AT III-thrombin association reaction by a factor of at least 2000 (Hoylaerts et al., J. Biol. Chem., 1984, 259, 5670–5677). Two forms of AT III (alpha and beta) exist in human plasma and have different affinities for heparin (Peterson and Blackburn, J. Biol. Chem., 1985, 260, 610–615; Brennan et al., FEBS LETT., 1987, 219, 431–436). Whereas AT IIIalpha, which occurs to the extent of 90–95% in plasma, has carbohydrate side-chains on the Asn residues 96, 135, 155 and 192, in AT IIIbeta only the positions 96, 155 and 192 are occupied. The physiological role of the two AT III forms is unknown.

The technique of directed mutagenesis permits the introduction of specific alterations into the AT III cDNA which lead to modifications in the amino acid composition of AT III. Methods for directed mutagenesis which use single-stranded DNA or heteroduplex DNA have been disclosed (Morinaga et al., BioTechnology, 1984, 7, 636–639; Kramer et al., Nucl. Acid Res., 198, 12, 9441–9456). Tab. 2 shows, by way of example, some oligonucleotides which have been employed for the directed mutagenesis of human AT III.

Mutants which have at one or more of the glycosylation sites Asn 96, Asn 135, Asn 155 and Asn 192 a different amino acid, preferably Gln, have now been prepared, which improves the heparin-binding/heparin-activating properties while retaining the protease specificity; in addition, mutants which have been modified at position Arg393 (preferably mutation to Met or Val) have been prepared which brings about a modification of enzyme specificity.

Mutants with improved heparin-binding/heparin-activating properties have advantages in AT III/heparin combination therapy because it is possible, where appropriate, to use lower heparin doses for the therapy.

On the other hand, specificity mutants result in new molecules in which the AT III property of possible heparin activation can be transferred to mutated molecules having affinity to new proteases (for example elastase, plasmin etc.), so that molecules of this type make it possible for therapy policies to be altered in an advantageous manner by reason of altered dosages.

Mutated AT III proteins can be expressed in mammalian cells, purified by standard methods and examined for their protease specificity or their heparin-activating properties, their biochemical/biophysical properties and/or their clinical parameters. The synthesis of modified forms of AT III is achieved by a vector/host cell system which rapidly leads to high expression rates (Zettlmeissl et al. (1988) Behring Inst. Mitt. 82, 26–34).

Accordingly, the invention relates to AT III mutants which (1) have at one or more of the glycosylation sites Asn 96, Asn 135, Asn 155 and Asn 192 a different amino acid, preferably Gln, (2) are modified at position Arg 393 (preferably mutation to Met or Val), (3) have a combination of mutations (1) and (2) which, as a rule, enhance the improvements.

The invention is furthermore described in the examples and in the patent claims.

Example 1

Synthesis of AT III mutants (general method)

A 1.4 kb fragment which contains the entire coding region of human AT III cDNA was isolated from the plasmid pbetaAT6 (EP 0 256 302 A2) by digestion with EcoRI/HindIII. This fragment was cloned into the polylinker (cleaved with EcoRI/HindIII) of the mutagenesis vector pMA 5–8. The resulting plasmid was called pMAATIII.

After the mutagenesis had been carried out (see description under "Mutagenesis"), the mutated cDNA was isolated by cutting with SacII/XbaI and cloned into the expression vector pAB 3-1 (AT III wild-type) which had likewise been digested with SacII/XbaI, which resulted in the plasmid pABmut. The pABmut plasmids carry the SV40 early enhanced/promoter unit, the SV40 polyadenylation site for early transcripts and the CMV immediate early enhancer (Zettlmeissl et al. loc. cit.) in addition to the particular mutated cDNA.

The pABmut plasmids were purified on CsCl gradients and cotransfected with with plasmids pSV2dhfr and pRMH140 in BHK cells (ATCC CCL10) as described by Zettlmeissl et al., loc. cit. The resistant clones (about 40–100) emerging after dual selection in DME medium+ 10% FCS+400 µg/ml G418 and 1 µM methotrexate (standard growth medium) were combined as clone mixture in T25 culture vessels. The mixed clones were expanded via T80 and T180 culture vessels in standard growth medium to plastic roller bottles (1750 $cm^2$) and cultured adherent therein to confluence. The confluent cells were washed twice with 200 ml of Iscove's medium (Behringwerke AG, Marburg) (for 2 hours at 37° C. in each case) and subsequently rolled with 500 ml of the same medium as harvest medium for 48 hours. The harvest medium was separated from cellular constituents by centrifugation. Aliquots of the conditioned harvest media were examined for their AT III antigen content in an ELISA specific for human AT III (Zettlmeissl et al. 1987, BioTechnology 5, 720–725). The levels of expression for wild-type AT III (AT III-WT) and various mutants measured in this way are shown by way of example in Tab. 3.

AT III-WT and mutated proteins derived therefrom were purified from the harvest media by a standard method (affinity chromatography using heparin-Sepharose, followed by fractional ammonium sulfate precipitation) (Zettlmeissl et al. 1987) and subsequently characterized.

Mutant AT III molecules can also be expressed using other expression vectors in various permanent mammalian cell lines in accordance with the state of the art.

Example 2

Mutagenesis/general method (Kramer et al., Nucl. Acids Res. (1984) 12, 9441–9456)

Single-stranded DNA of the mutagenesis vector pMAATIII which had been transformed in the E. coli strain WK6 was isolated by standard methods.

Plasmid DNA of pMC5-8 was cut with EcoRI/HindIII, and the vector fragment (3.8 kb) was purified from an agarose gel by paper solution (Maniatis et al. 1982, Molecular Cloning—A Laboratory Manual, Cold Spring Harbor, N.Y.).

To prepare a gapped duplex DNA, 0.1 pmol of double-stranded fragment (from pMC) and 0.5 pmol of single-stranded DNA (pMAATIII) were heated in 12.5 mM Tris-HCl pH 7.5+190 mm KCl (final volume 40 µl) at 100° C. for 4 minutes and subsequently incubated at 65° C. for 10 minutes. To hybridize on the mutagenesis oligonucleotide (see Tab. 2) 8 µl of the said hybridization solution were heated with 4–8 pmol (2 µl) of the enzymatically phosphorylated oligonucleotide at 65° C. for 5 minutes and then slowly cooled to room temperature. Addition of 24 µl of $H_2O$, 4 µl of 10×fill-in buffer (625 mM KCl, 275 mM Tris-HCl pH 7.5, 150 mM $MgCl_2$, 20 mM DTT, 0.5 mM ATP and 0.25 mM of each of the four dNTPs), 1 µl of T4 DNA ligase (5 U/µl) and 1 µl of Klenow fragment of DNA polymerase I (1 U/µl) and followed by incubation at room temperature for 45 minutes. 5 µl of filled-in gapped duplex DNA were transformed into WK6 muts (mutS215:Tn10). The entire transformation mixture is grown in a shake culture in LB medium+25 µg/ml chloramphenicol (10 ml) at 37° C. overnight. The plasmid DNA was purified from the entire mixture by standard methods (Maniatis et al. 1982). About 20 ng of the purified plasmid were transformed into WK6. The transformants were selected on LB plates containing 25 µg/ml chloramphenicol.

Five of these transformants were analyzed for the desired mutation by a suitable sequence reaction (C-, T-, A- or G-specific). Positive clones were verified by detailed sequence analysis in the region of the mutagenesis site (Sanger et al. (1988), Proc. Natl. Acad. Sci. USA 74, 5463–5467).

Example 3

AT III - Met 393: AT III - Val 393 and AT III - Leu 393

With the aim of generating a molecule with specificity similar to alpha1 antitrypsin (elastase inhibitor), Arg393 of AT III (P1 position) was converted into a Met, Val or Leu. Oligonucleotides Nos. 1, 2 and 3 from Tab. 2 were employed for the mutagenesis.

The mutants are synthesized and released into the culture medium by BHK cells in amounts comparable to AT III wild-type (WT) (Tab. 4), show a behavior towards anti-AT III sera from rabbits which is identical to AT III plasma and AT III-WT, and can be purified to purities greater than 95% by the standard method described above in analogy to AT III-WT. These mutants do not differ from AT III-WT in the binding and elution behavior on heparin-Sepharose. This indicates that the heparin-binding and heparin-activating behavior of the mutants is intact.

The mutants no longer have progressive inhibitory (Hensen et al., 1963, Thromb. Diatl. Haemorrh. 9, 18–29) or heparin cofactor activity (Schrader et al., 1986, Ärztl. Lab. 32, 111–114) towards thrombin (Tab. 3).

In contrast to AT III-WT, the three mutants inhibit leukocyte elastase. The elastase was isolated from human leukocytes by the method described by Engelbrecht et al. (Hoppe-Seyler's Ztschr. Physiol. Chemie 363, 305–315, 1982). The substrate used was the MeO-Suc-Ala-Ala-Pro-Val-pNA (Calbiochem) described by Nakajima et al. (J. Biol. Chem. 254, 4027–4032, 1979). The liberation of the paranitroaniline from the substrate was measured in a spectrophotometer as the increase in absorption at 405 nm within 15 min. This absorption was defined as 100% activity of the PMN elastase enzyme. The inhibitors were preincubated in concentrations increasing up to a maximum of 100 µg/ml with the enzyme for one hour. The enzyme reaction was then started with the substrate. The assay was carried out in 0.1 mol/l HEPES, pH 7.5, +0.1 mol/l sodium chloride. The substrate concentration was 0.13 mmol/l. The IC50 was defined as the inhibitor concentration, in µg/ml, which inhibited 50% of the enzyme activity. Substances which showed no inhibiting action at a maximum concentration of 100 µg/ml were designated inactive. The reference inhibitor used was alpha1 protease inhibitor (alpha1 PI, alpha1 antitrypsin), which has an inhibition value of 3.7. At III-WT showed no inhibition of PMN elastase activity. AT III Val showed an activity of 4.0 µg/ml, comparable to alpha1 PI, whereas AT III Met and AT III Leu were distinctly less active, with 28 and 65 mg/ml respectively (see Table which follows).

The described PMN elastase assay was used to determine the KI for AT III-Val 393 by comparison with alpha1 PI. The concentrations of the substrate MeO-Suc-Ala-Ala-Pro-Val-pNA employed were 0.0011, 0.0022, 0.0044, 0.0087, 0.0175, 0.035, 0.7 mmol/l. The concentration of the inhibitor was $3.5 \times 10^{-8}$ mol/l.

In both cases the inhibition of PMN elastase is a non-competitive inhibition (see Table which follows). The KI values for alpha1 PI and AT III-Val 393 are virtually identical.

Example 4

AT III-Gln135 and AT III-Gln155

One aim of the experiments claimed in this application as invention is to examine the effect of glycosylation in the AT III molecule on the biological and biochemical properties of AT III. Asn→Gln exchanges in positions 135 and 155 were used to generate two AT III mutants (AT III-Gln135 and AT III-Gln155) each of which lacked a carbohydrate side-chain. The mutagenesis oligonucleotides employed were oligonucleotides 8 and 9 (Tab. 2). The expression rates for both mutants in BHK cells (AT III in the culture medium) are, as shown in Tab. 4, of the same order of magnitude as for AT III-WT. Both mutants show a behavior towards anti-AT III sera from rabbits which is identical to AT III plasma and AT III-WT, with respect to specific progressive inhibitory and heparin cofactor activity (Tab. 4), and can be purified to purities greater than 95% by the standard method described above.

The two mutants were examined for their relative ability to inactivate thrombin as a function of the heparin concentration in the assay and compared with AT III plasma, AT III-WT and the mutant AT III-Lys49 (Tab. 5).

The assay was carried out under the following conditions: 0.02 U (antigen)/ml AT III (AT III plasma, AT III-WT or AT III-Mut) was preincubated with 0.3 IU/ml alpha-thrombin (human), 2 KIU/ml aprotinin (Behringwerke) and heparin (Hoffmann-LaRoche) in concentrations of 0-25 IU/ml in a volume of 1 ml at 37° C. for 5 minutes. After addition of 100 µl of substrate reagent (2 mM HD-CHA-But-Arg-pNA), the change in extinction at 405 nm (37° C.) was followed kinetically. The maximum inhibition of alpha-thrombin at heparin saturation was set equal to 100%.

The inhibition of thrombin at low heparin concentrations by the mutants AT III-Gln135 and AT III-Gln155 is better than that of AT III plasma and AT III-WT (Tab. 5).

Tab. 5 indicates the heparin concentration at half-maximum thrombin inhibition (c ½) for AT III plasma, AT III-WT and various AT III mutants.

Example 5
AT III-Gln135/155

The mutations described in Example 4 were combined in one AT III molecule by sequential mutagenesis with oligo-nucleotides 8 and 9 (Tab. 2). The mutated protein behaves like a recombinant wild-type AT III molecule in the standard purification method described.

The improved inhibition of alpha-thrombin at low heparin concentrations found with AT III-Gln135 and with AT III-Gln155 is even more pronounced in the case of AT III-Gln135/155 (Tab. 5).

TABLE 3-continued

Inhibition of elastase from human polymorphonuclear granulocytes (PMN elastase)

| Substance | $IC_{50}$ (µg/ml) | $k_I$ (mol/l) |
|---|---|---|
| AT III - Val 393 | 4.0 | $1 \times 10^{-8}$ |
| AT III - Leu 393 | 65.0 | n.d. |

— = no inhibition ($IC_{50}$ > 100 µg/ml)
n.d. = not determined

TABLE 4

Expression and purification of AT III mutants

| | Conc. in roller supernatants[1] (mg/l) | Purification by standard method | $PI^{[2]}$ (U/mg) | $HC^{[3]}$ (U/mg) |
|---|---|---|---|---|
| ATIII-Plasma | — | +++ | 4-6.5* | 4-6.5* |
| ATIII-WT | 4.2 | +++ | 6.2 | 5 |
| ATIII-Met393 | 5.5 | +++ | 0 | 0 |
| ATIII-Val393 | 4.8 | +++ | 0 | 0 |
| ATIII-Leu393 | 9.8 | +++ | 0 | 0 |
| ATIII-Thr394 | 9.7 | +++ | n.d. | 3.5 |

TABLE 1

| 1 | HGSPVDICTA | KPRDIPMNPM | CIYRSPEKKA | TEDEGSEQKI | PEATNRRVWE |
|---|---|---|---|---|---|
| 51 | LSKANSRFAT | TFYQHLADSK | NDNDNIFLSP | LSISTAFAMT | KLGACNDTLQ |
| 101 | QLMEVFKFDT | ISEKTSDQIH | FFFAKLNCRL | YRKANKSSKL | VSANRLFGDK |
| 151 | SLTFNETYQD | ISELVYGAKL | QPLDFKENAE | OSRAAINKWV | SNKTEGRITD |
| 201 | VIPSEAINEL | TVLVLVNTIY | FKGLWKSKFS | PENTRKELFY | KADGESCSAS |
| 251 | MMYQEGKFRY | RRVAEGTQVL | ELPFKGDDIT | MVLILPKPEK | SLAKVEKELT |
| 301 | PEVLQEWLDE | LEEMMLVVHM | PRFRIEDGFS | LKEQLQDMGL | VDLFSPEKSK |
| 351 | LPGIVAEGRD | DLYVSDAFHK | AFLEVNEEGS | EAAASTAVVI | AGRSLNPNRV |
| 401 | TFKANRPFLV | FIREVPLNTI | IFMGRVANPC | VK | |

TABLE 2

Examples of mutagenesis of oligonucleotides

| No. | Sequence | Mutation |
|---|---|---|
| 1 | 5' GGG GTT TAG CGA CAT GCC AGC AAT CAC 3' | Arg393-Met |
| 2 | 5' GGG GTT TAG CGA AAC GCC AGC AAT CAC 3' | Arg393-Val |
| 3 | 5' GGG GTT TAG CGA AAG GCC AGC AAT CAC 3' | Arg393-Leu |
| 4 | 5' GGG GTT TAG CGT ACG GCC AGC 3' | Ser394-Thr |
| 5 | 5' GGG GTT TAG CAT ACG GCC AGC 3' | Ser394-Met |
| 6 | 5' GGA CAG TTC CTT GAC ACG CCG G 3' | Trp49-Lys |
| 7 | 5' G GAG GGT GTC CTG ACA GGC ACC CAG C 3' | Asn96-Gln |
| 8 | 5' GGA GGA TTT CTG GGC TTT TCG | Asn135-Gln |
| 9 | 5' G GTA GGT CTC CTG GAA GGT AAG G 3' | Asn155-Gln |
| 10 | 5' CG GCC TTC GGT CTT CTG GGA CAC CC 3' | Asn192-Gln |

TABLE 3

Inhibition of elastase from human polymorphonuclear granulocytes (PMN elastase)

| Substance | $IC_{50}$ (µg/ml) | $k_I$ (mol/l) |
|---|---|---|
| alpha, PI | 3.7 | $1.7 \times 10^{-8}$ |
| AT III - WT | — | n.d. |
| AT III - Met 393 | 28.0 | n.d. |

TABLE 4-continued

Expression and purification of AT III mutants

| | Conc. in roller supernatants[1] (mg/l) | Purification by standard method | $PI^{[2]}$ (U/mg) | $HC^{[3]}$ (U/mg) |
|---|---|---|---|---|
| ATIII-LYS49 | 3.3 | ++ | 4.6 | 4.3 |
| ATIII-Gln135 | 8 | +++ | 3.9 | 4.5 |

TABLE 4-continued

Expression and purification of AT III mutants

| | Conc. in roller supernatants[1] (mg/l) | Purification by standard method | PI[2] (U/mg) | HC[3] (U/mg) |
|---|---|---|---|---|
| ATIII-Gln155 | 3.6 | +++ | 4.2 | 5.5 |
| ATIII-Gln135/155 | 1.2 | +++ | n.d. | 3.8 |

[1] 40 h serum-free supernatants (ELISA) of BHK cells
[2] progressive inhibitory activity (Hensen et al. 1963)
[3] heparin cofactor activity (Schrader et al. 1986)
n.d. = not determined
*batch-dependent range of variation

TABLE 5

Dependence of thrombin inactivation on the heparin concentration

| | $C_{1/2}$ Heparin[1] (mIU/ml) |
|---|---|
| ATIII-Plasma | 65 |
| ATIII-WT | 65 |
| ATIII-Gln135 | 22 |
| ATIII-Gln155 | 22 |
| ATIII-Gln135/155 | 5 |
| ATIII-Lys49 | greater than 360 |

[1] heparin concentration at half-maximum relative thrombin inhibition

We claim:

1. An antithrombin III (AT III) mutant, which contains an amino acid substitution at position 49, 96, 135, 155, 192, 393, or 394, wherein the substitution can be present either singly or in combination with one or more other substitutions, and wherein the amino acid substituted at position 393 is not His.

2. A method for the preparation of one of the mutants as claimed in claim 1, which comprises inserting a DNA coding for the mutant of AT III into an appropriate expression vector and expressing said mutant.

3. A pharmaceutical composition comprising one or more of the mutants as claimed in claim 1 together with a physiologically acceptable auxiliary or excipient.

4. A method for the preparation of an antithrombin III (AT III) mutant, which contains an amino acid substitution at position 96, 135, 155, 192, or 393, wherein the substitution can be present either singly or in combination with one or more other substitutions, and wherein the amino acid substituted at position 393 is not His, which comprises inserting a DNA coding for the mutant of AT III into an appropriate expression vector and expressing said mutant.

5. A method for the preparation of an antithrombin III (AT III) mutant wherein a Lys amino acid is substituted for Trp at position 49, which comprises inserting a DNA coding for the mutant of AT III into an appropriate expression vector and expressing said mutant.

* * * * *

UNITED STATES PATENT AND TRADEMARK OFFICE
CERTIFICATE OF CORRECTION

PATENT NO. : 5,700,663
DATED : December 23, 1997
INVENTOR(S) : Gerd Zettlmeissl, et. al.

It is certified that error appears in the above-indentified patent and that said Letters Patent is hereby corrected as shown below:

Title page, item [54] and col. 1, line 1, should read -- ANTITHROMBIN --.

Signed and Sealed this

Twenty-eighth Day of July, 1998

Attest:

BRUCE LEHMAN

*Attesting Officer*  *Commissioner of Patents and Trademarks*